United States Patent [19]

Blank et al.

[11] 4,053,526

[45] Oct. 11, 1977

[54] PROCESS FOR ISOLATING DINITRONAPHTHALENES

[75] Inventors: Heinz Ulrich Blank, Odenthal; Friedrich Durholz, Remscheid; Guido Skipka, Leverkusen, all of Germany

[73] Assignee: Bayer Aktiengesellschaft, Leverkusen, Germany

[21] Appl. No.: 672,689

[22] Filed: Apr. 1, 1976

[30] Foreign Application Priority Data

Apr. 19, 1975 Germany .............................. 2517437

[51] Int. Cl.$^2$ .............................................. C07C 79/10
[52] U.S. Cl. ...................................... 260/645; 260/705
[58] Field of Search .................................. 260/645, 705

[56] References Cited

PUBLICATIONS

Donaldson, The Chemistry and Technology of Naphthalene Compounds, Edward Arnold (Publishers) Ltd., London, 1958, pp. 150 to 153.
Urbanski, Chemistry and Technology of Explosives, vol. I, The MacMillan Co., New York, 1964, pp. 428 and 429.
Waag, German Auslegeschrift 1,179,545, Oct. 1964.

*Primary Examiner*—Leland A. Sebastian
*Attorney, Agent, or Firm*—Burgess, Dinklage & Sprung

[57] ABSTRACT 1,5- and 1,8-dinitronaphthalenes are isolated from mixtures of isometric dinitronaphthalenes at least containing the same. The mixture of isomers is treated successively with a more polar solvent and a less polar aromatic solvent for dinitronaphthalenes thereby dissolving the mixture of isomers except for 1,5-dinitronaphthalenes which remains largely undissolved in the more polar solvent. The residual mixture of isomers is subsequently treated, after removal of the more polar solvent, with a less polar aromatic solvent at elevated temperatures in which 1,8-dinitronaphthalenes remains as a largely insoluble residue.

16 Claims, No Drawings

PROCESS FOR ISOLATING DINITRONAPHTHALENES

BACKGROUND

This invention relates to a process for isolating 1,5-and 1,8-dinitronaphthalene from a mixture of isomeric dinitronaphthalenes.

It is known that mixtures of isomeric dinitronaphthalenes are obtained when naphthalene is nitrated, for example with a mixture of concentrated nitric acid and sulphuric acid (Houben-Weyl, Methoden der organischen Chemie (Methods of Organic Chemistry), volume 10/1, page 494 (1971)). A number of methods are known for obtaining 1,5-and 1,8-dinitronaphtahlene from these mixtures. Thus it is possible, for example, to dissolve the mixtures in ethylene dichloride and, by fractional cooling, to deposit and separate off from the hot solution first the 1,5 component at 50° C and then, after concentrating the filtrate, the 1,8 component at room temperature (German Published Specification No. 1,618,109). Differences in the solubilities of the two dinitronaphthalenes in organic solvents are also used in two further known processes for the separation of such mixtures, the solvents used being dimethylformamide (French Pat. No. 1,320,250) and acetone (Japanese Patent Application No. 2551/66). In Chemisches Zentralblatt (1938), volume I, page 587, a process is described according to which 1,8-dinitronaphthalene is purified by recrystallisation from benzene or acetic anhydride. From Chemical Abstracts, volume 43 (1949), page 6190, a process is known which utilises the differences in the solubilities of the two dinitronaphtalenes in concentrated sulphuric acid for a separation. Moreover, it is known from German Published Specification No. 1,618,109 partially to dissolve the mixture of isomers in nitric acid and then to effect fractional deposition of the components by cooling and diluting with water.

SUMMARY

A process for isolating 1,5- and 1,8-dinitronaphthalene from mixtures of isomeric dinitronaphthalenes which contain at least the two constituents has been found, according to which the mixture of isomers is treated successively with a more polar solvent and a less polar aromatic solvent for dinitronaphthalenes, the mixture of isomers first being dissolved, except for 1,5-dinitronaphthalene, which remains largely undissolved, in the more polar solvent and subsequently the residual mixture of isomers being so treated, after removal of the more polar solvent, with a less polar aromatic solvent at elevated temperature that 1,8-dinitronaphthalene remains as a largely insoluble residue.

DESCRIPTION

Both mixtures which consist only of 1,5- and 1,8-dinitronaphthalene and mixtures which, in addition to 1,5- and 1,8-dinitronaphthalene, also contain impurities can be employed for the process according to the invention. Possible impurities are essentially the other dinitronaphthalenes, mono- and tri-nitronaphthalenes and resinous residues. The proportion of impurities in the 1,5-/1,8-dinitronaphthalene mixture should in general be not greater than 30% and preferably less than 20%.

The mixtures of dinitronaphthalenes, such as can be employed for the process according to the invention, contain, for example, at least 10%, preferably at least 20%, and at most 98% of 1,5-dinitronaphthalene and at least 2%, preferably at least 5% and at most 90% of 1,8-dinitronaphthalene.

A mixture of isomeric dinitronaphthalenes is formed, for example, when naphthalene is nitrated with concentrated sulphuric acid and nitric acid; using this mode of preparation, a mixture is obtained which essentially consists of 1,5- and 1,8-dinitronaphthalene and resinous residues as the end products (BIOS Report 1152, page 45).

Solvents which can be used as more polar solvents for the process according to the invention are, for example, compounds with a dielectric constant at 20° C of from about 6 to 200, preferably from 7 to 75 and preferentially from 10 to 60. Examples of more polar solvents which may be mentioned are straight-chain or branched $C_1$ to $C_6$ alkylsulphones, such as dimethylsulphone, ethyl-butyl-sulphone, methyl-ethylsulphone, ethyl-tert.-butyl-sulphone, propyl-iso-pentylsulphone and methyl-hexylsulphone, cyclic sulphones of the formula

I wherein
$n$ can be a number from 3 to 7,
such as thia-cyclopropyl-1,1-dioxide, thia-cyclobutyl-1,1-dioxide (sulpholane), thia-cyclopentyl-1,1-dioxide, thia-cyclohexyl-1,1-dioxide, thia-cycloheptyl-1,1-dioxide and thia-cyclooctyl-1,1-dioxide, lactams of the formula

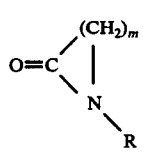

II wherein
$m$ can be a number from 3 to 8 and
R can be hydrogen or a $C_1$ to $C_6$ alkyl radical,
such as ε-caprolactam and N-methylpyrrolidone, carboxylic acid amides, such as N,N-dimethylformamide, N-methylformanilide, formanilide and acetamide, and N,N-dimethylacetamide, halogenated aliphatic hydrocarbons with 1 to 6 carbon atoms, such as methylene chloride, 1,2-dichloroethane, 1,1,2,2-tetrachloroethane, 1,1,1-trichloroethane and 1,2-dichloropropane, and ketones of the formula

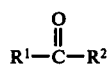

III wherein
$R^1$ and $R^2$ are identical or different and represent straight-chain or branched $C_1$ to $C_6$ alkyl radicals or are linked via the group

IV wherein
$o$ represents the numbers 4, 5 or 6, to form a ring, which optionally can be substituted by $C_1$ to $C_3$ alkyl radicals, such as acetone, methyl ethyl ketone, iso-propyl butyl ketone, dipentyl ketone, iso-hexyl methyl ketone, cyclopentyl-ketone, cyclohexyl-ketone, cycloheptyl-ketone, 3,4-dimethylcyclohexylketone and 4-ethylcyclohexylketone.

Examples of more polar solvents which may be mentioned in addition are chlorobenzene, o-dichlorobenzene, 4-chlorotoluene, 3,4-dichlorotoluene, 1,1,2-trichloroethane, nitrobenzene, o-nitrotoluene, m-nitrotoluene, p-nitrotoluene, nitromethane, o-nitrochlorobenzene, m-nitrochlorobenzene, p-nitrochlorobenzene, 1,2-nitro-ethylbenzene, aniline, o-toluidine, m-toluidine, N-methyl-aniline (containing water), N,N-dimethylanilin (containing water), N,N-diethylamiline, foranilide, benzonitrile, toluonitrile, acetonitrile β-hydroxypropionitrile, dimethylsulphoxide, diphenylsulphoxide and ethyl acetate.

Solvents which are preferred as more polar solvents for the process according to the invention are sulpholane, ε-caprolactam and acetone.

The more polar solvents can be employed either individually or as mixtures. It is also possible for the more polar solvents to contain water.

Solvents which may be mentioned as less polar aromatic solvents for the process according to the invention are compounds which at 20° C have a dielectric constant of from 1.5 to 5.5, preferably from 2 to 5 and preferentially from 2.2 to 4.5. Examples of less polar solvents which may be mentioned are aromatic compounds of the formula

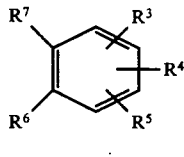

V wherein
$R^3$, $R^4$ and $R^5$ are identical or different and represent hydrogen, chlorine or $C_1$ to $C_6$ alkyl radicals and $R^6$ and $R^7$ are identical or different and represent hydrogen or $C_1$ to $C_6$ alkyl radicals or, conjointly with the groups $$-(CH_2)_4- \text{ or } -(CH=CH)_2-  \qquad VI$$

are linked to form a ring, which optionally is substituted by methyl and/or ethyl groups,
such as benzene, toluene, xylene, ethylbenzene, cumene, tetralin, diethylbenzene, o-methylethylbenzene, n-propylbenzene, dipropylbenzene, 1,2,4-trimethylbenzene, m-ethyl-toluene, p-ethyl-toluene, m-methyl-isopropylbenzene, p-methyl-ethylbenzene, 1,2-dimethyl-4-ethylbenzene, 1,2,4-triethylbenzene, 1-methylbnaphthalene, p-dichlorobenzene, 1-chloronaphthalene, 1,2,4-trichlorobenzene and 2-chlorotoluene, and aromatic esters, such as anisole, phenetole, diphenyl ether, tolyl methyl ether and ditolyl ether.

Solvents which are preferred as less polar aromatic solvents for the process according to the invention are toluene and xylene.

The less polar aromatic solvents can be used either individually or as mixtures.

In a particular embodiment of the process according to the invention 1,5-dinitronaphthalene is separated off by treatment with sulpholane and 1,8-dinitronaphthalene is separated off by treatment with toluene.

The process according to the invention can be carried out as follows:

In a first stage the mixture of dinitronaphthalenes formed during the nitration of naphthalene or 1-nitronaphthalene is taken up with a more polar solvent. The mixture of dinitronaphthalenes can be employed without further working up and drying.

The amount of more polar solvent and, if appropriate, the amount of water and the temperature are so selected that all the by-products and the 1,8-dinitronaphthalene are completely dissolved and only 1,5-dinitronaphthalene remains as the residue. The 1,5-dinitronaphthalene can be separated off in a manner which is in itself known, for example by filtration.

In general, the separation is effected at a temperature of from 20° to 150° C, preferably from 40° to 110° C, and at pressures of from 0.1 to about 5 bars, preferably at 0.5 to 1.5 bars.

The amount of more polar solvent which is employed for the separation by the process according to the invention is 1.2 to 20 times the amount, preferably 1.4 to 15 times the amount, of 1,8-dinitronaphthalene present in the mixture.

In general, the water content of the mixture to be separated should be not greater than 50% by weight. Excess water can be removed from the mixture to be separated by distillation.

In a preferred embodiment of the process according to the invention a water content of 0.1 to 25% by weight, preferably b 0.5 to 20% by weight and preferentially 1.5 to 15% by weight in the total mixture is used when separating off 1,5-dinitronaphthalene.

After separating off the 1,5-dinitronaphthalene which did not dissolve in the more polar solvent, the isomeric dinitronaphthalenes which have not been separated off can be obtained as a solid from the more polar solvent. The solid can be isolated, for example, by distilling off the more polar solvent.

In the second stage of the process according to the invention the dinitronapthalenes which could not be separated off with the aid of the more polar solvent are treated with a less polar aromatic solvent. The amount of the less polar aromatic solvent and the temperature are so selected that all the by-products are completely dissolved and only 1,8-dinitronaphthalene remains as the residue.

In a particularly advantageous embodiment of the process it is possible to dispense with intermediate isolation of the isomeric dinitronaphthalenes by adding a higher-boiling less polar aromatic solvent to the solution of isomeric dinitronaphthalenes in the more polar solvent which remains after separating off the 1,5-dinitronaphthalene and then distilling off the more polar solvent.

In general, the separation is effected at a temperature of from 40° to 150° C, preferably from 50° to 130° C and preferentially at 70° to 100° C and at pressures between 0.1 and 5 bars, preferably at 0.5 to 1.5 bars.

The amount of the less polar aromatic solvent is 1 to 20 times the amount, preferably 2.5 to 7 times the amount, of 1,8-dinitronaphthalene present in the mixture.

1.8-Dinitronaphthalene, which has not dissolved in the less polar aromatic solvent, is separated off in a manner which is in itself known, for example by filtration.

A residue which still contains amounts of 1,5- and 1,8-dinitronaphthalene is obtained from the less polar aromatic solvent. Part or a substantial amount of the residue can be employed again in a new separation.

The process according to the invention can be carried out both discontinuously and continuously.

When carrying out the process according to the invention continuously, the mixture of dinitronaphthalenes is treated successively with a more polar solvent and a less polar aromatic solvent for dinitronaphthalenes and, in a first process stage, the mixture of dinitronaphthalenes is dissolved in the more polar solvent and only 1,5-dinitronaphthalene remains largely undissolved and, in a second process stage, the residual mixture of dinitronaphthalenes is treated, after removal of the more polar solvent, with a less polar aromatic solvent at elevated temperature, in such a way that 1,8-dinitronaphthalene largely remains as an insoluble residue and, after separating off the less polar aromatic solvent, the residual mixture of dinitronaphthalenes is fed back into the first process stage. A substantial amount or part of the dinitronaphthalenes can be fed back into the first process stage.

The process according to the invention makes it possible to prepare 1,5- and 1,8-dinitronaphthalene in high yields. The dinitronaphthalenes thus obtained are virtually free from isomeric impurities.

1,5- and 1,8-dinitronaphthalene can be reduced to the corresponding amino compounds (BIOS 1152, No. 22, pages 48 to 54). The amino compounds are intermediate products for dyestuffs and polyurethanes.

EXAMPLE 1

480 g of a dinitronaphthalene mixture comprising 57.2% by weight of 1,8-dinitronaphthalene, 38.7% by weight of 1,5-dinitronaphthalene, 1.5% by weight of 1,6-dinitronaphthalene, 0.3% by weight of 1,7-dinitronaphthalene, 1.5% by weight of 1-nitronaphthalene and 0.3% by weight of isomeric trinitronaphthalenes are suspended in 1,500 ml of acetone and the suspension is heated under reflux for 1.5 hours. It is then cooled to 57° C and filtered under a slight vacuum and the material on the filter is washed with a total of 450 ml of acetone. 130.7 g of 99.5% pure 1,5-dinitronaphthalene of melting point 216° to 217° C are obtained.

The filtrate and the washing acetone are combined and concentrated to dryness in a rotary evaporator. The resulting solid product is suspended in 1,220 ml of toluene and the suspension is warmed to 100° C and, after cooling to 70° C, stirred for a further 30 minutes. 1,8-Dinitronapthalene, which has precipitated, is isolated using a heated suction filter, washed with 500 ml of toluene and sucked dry in air. 194.0 g of 99.6% pure 1,8-dinitronaphthalene of melting point 170° to 171° C are obtained.

88.9 g of a dinitronaphthalene mixture crystallise out of the filtrate on cooling to 0° C and are fed back into the crystallisation process. The residue (63 g) remaining after distillation of the toluene is discarded.

EXAMPLE 2

480 g of a dinitronaphthalene mixture comprising 57.2% by weight of 1,8-dinitronaphthalene, 38.7% by weight of 1,5-dinitronaphthalene, 1.5% by weight of 1,6-dinitronaphthalene, 0.3% by weight of 1,7-dinitronaphthalene, 1.5% by weight of 1-nitronaphthalene and 0.3% by weight of isomeric trinitronaphthalenes are suspended in 1,500 ml of acetone and the suspension is heated under reflux for 1.5 hours. It is then cooled to 57° C and the material which has not dissolved is filtered off under a slight vacuum and washed with a total of 450 ml of acetone. 130.1 g of 99.4% pure 1,5-dinitronaphthalene of melting point 216° to 217° C are obtained.

The filtrate and the acetone are combined and about half of the acetone is distilled off, 700 ml of xylene are then added and the remainder of the acetone is distilled off via a 50 cm column with a dephlegmator. On cooling to 90° C, 1,8-dinitronaphthalene crystallises out of the xylene solution and is filtered off and washed with 300 ml of xylene. 185.5 g of 99.6% pure 1,8-dinitronaphthalene of melting point 170° to 171° C are obtained.

The xylene solution is concentrated to about 400 ml and cooled to room temperature. 124.6 g of a 1,5-/1,8-dinitronaphthalene mixture are isolated by filtering off and are fed back into the crystallisation process. The by-products remain dissolved in the xylene and are removed with this from the process cycle.

EXAMPLE 3

260 g of a dinitronaphthalene mixtuure comprising 60.3% by weight of 1,8-dinitronaphthalene, 33.3% by weight of 1,5-dinitronaphthalene, 1.0% by weight of 1.6-dinitronaphthalene, 0.6% by weight of 1,7-dinitronaphthalene, 1.7% by weight of 1,3,8-trinitronaphthalene, 0.8% by weight of 1,4,5-trinitronaphthalene, <0.1% by weight of 1,3,5-trinitronaphthalene and 1.0% by weight of mononitronaphthalene are suspended in 400 ml of aqueous ε-caprolactam (water content 20% by weight) and the suspension is heated to the boil. It is then left to cool to 90° C and stirred for a further 30 minutes at this temperature, the material which has not dissolved is then separated off using a heated suction filter and is washed first with 290 ml of aqueous ε-caprolactam (80% strength) and then with 740 ml of water. After drying, 61.1 g of 99.5% pure 1,5-dinitronaphthalene of melting point 217° C are obtained.

The washing water and the filtrate are combined and the product which has precipitated is filtered off, washed with 500 ml of water and suspended in 700 ml of toluene. The suspension is heated to the boil and the water is separated off azeotropically in a water separator. The mixture is then allowed to cool to 70° C and the crystals which have precipitated are filtered off using a heated suction filter, washed with 240 ml of toluene and dried by sucking air through the crystals. 110 g of 99.6% pure 1,8-dinitronaphthalene of melting point 171° to 172° C are obtained.

After cooling to 0° C, 49.4 g of a dinitronaphthalene mixture cystallise out of the filtrate.

EXAMPLE 4

678 g of a water-moist dinitronaphthalene mixture comprising 57.9% by weight of 1,8-dinitronaphthalene, 40.1% by weight of 1,5-dinitronaphthalene, 0.1% by weight of 1,6-dinitronaphthalene, 0.1% by weight of 1,7-dinitronaphthalene, 0.1% by weight of 1,3,8-trinitronaphthalene, 0.1% by weight of 1,4,5-trinitronaphthalene, 0.1% by weight of 1,3,5-trinitronaphthalene and 1% by weight of mononitronaphthalene are suspended in 500 ml of sulpholane (95% strength). Water is then distilled off until the sump temperature reaches 129° C, the suspension is then cooled to 80° C and stirred for 30 minutes at this temperature and 1,5-dinitronaphthalene, which has precipitated, is separated off using a heated suction filter. The filter cake is washed first with 290 ml of aqueous sulpholane (95% strength)

and then with 1,100 ml of water. After drying, 128.4 g of 99.4% pure 1,5-dinitronaphthalene of melting point 216° to 217° C are obtained.

The washing water and the filtrate are combined and crude 1,8-dinitronaphthalene, which has precipitated, is filtered off and washed with 500 ml of water. The moist filter cake is suspended in 1,260 ml of toluene and the water is separated off by azeotropic distillation in a water separator. The suspension is then cooled to 70° C and stirred for 30 minutes at this temperature and 1,8-dinitronaphthalene is filtered off using a heated suction filter and washed with 300 ml of toluene. 182.5 g of 99.5% pure 1,8-dinitronaphthalene of melting point 170° to 171° C are obtained.

At 0° C 83.2 g of a 1,5-/1,8-dinitronaphthalene mixture crystallise out of the filtrate. After distilling the water from the aqueous sulpholane mother liquor, the sulpholane can be used again for crystallisations.

EXAMPLE 5

150 g of dinitronaphthalene comprising 60.1% by weight of 1,5-dinitronaphthalene, 39.3% by weight of 1,8-dinitronaphthalene, 0.2% by weight of 1,6-dinitronaphthalene, 0.2% by weight of 1-nitronaphthalene and 0.2% by weight of unidentified compounds are suspended in 430 ml of 1,2-dichloroethane and the suspension is heated under reflux for 1 hour whilst stirring. After cooling to 52° C, the suspension is stirred for 10 minutes and 1,5-dinitronaphthalene, which has crystallised out, is filtered off using a heated suction filter and washed with 300 ml of 1,2-dichloroethane. 78.8 g (corresponding to a yield of 87.4%) of 99.5% pure 1,5-dinitronaphthalene are obtained.

1,2-Dichloroethane is distilled in vacuo and the resulting residue is suspended in 740 ml of cumene. The suspension is warmed at 120° C until the dinitronaphthalene mixture has dissolved and the solution is then cooled to 80° C and stirred for 30 minutes at this temperature. The residue, consisting of 1,8-dinitronaphthalene which has not dissolved, is then filtered off using a suction filter heated to 80° C and is washed with 200 ml of cumene. After drying, 40.4 g of 99.4% pure 1,8-dinitronaphthalene are obtained.

The filtrate is concentrated to 150 ml by distilling off the cumene. 28.5 g of a mixture consisting of 1,8-and 1,5-dinitronaphthalene settles out at room temperature.

The 28.5 g of the mixture of 1,5- and 1,8-dinitronaphthalene thus obtained is again suspended in 1.3 ml of 1,2-dichloroethane and the suspension is heated under reflux for 15 minutes whilst stirring. After cooling to 52° C, the suspension is stirred for 10 minutes and 1,5-dinitronaphthalene, which has crystallised out, is separated off using a heated suction filter. The 1,5-dinitronaphthalene which has been separated off is washed with 50 ml of 1,5-dichloroethane. 7.2 g of 99.2% pure 1,5-dinitronaphthalene are obtained.

1,2-Dichloroethane is distilled off in vacuo and the resulting residue is suspended in 230 ml of cumene. The suspension is warmed to 120° C until the dinitronaphthalene mixture has dissolved and the solution is then cooled to 80° C and stirred for 30 minutes at this temperature. 1,8-Dinitronaphthalene, which has not dissolved, is separated off using a suction filter warmed to 80° C and is washed with 50 ml of cumene. After drying, 12 g of 99.4% pure 1,8-dinitronaphthalene are obtained.

What is claimed is:

1. Process for isolating 1,5- and 1,8-dinitronaphthalene from mixtures of isomeric dinitronaphthalenes at least containing the same which comprises treating the mixture of isomers successively with a more polar solvent and a less polar aromatic solvent for dinitronaphtalenes thereby dissolving the mixture of isomers except for 1,5-dinitronaphthalene which remains largely undissolved in the more polar solvent, and subsequently treating the residual mixture of isomers, after removal of the more polar solvent, with a less polar aromatic solvent at elevated temperature in which 1,8-dinitronaphthalene remains as a largely insoluble residue.

2. Process of claim 1 wherein compounds which at 20° C have a dielectric constant of 6 to 200 are used as the more polar solvent.

3. Process of claim 1 wherein compounds which at 20° C have a dielectric constant of from 7 to 75 are used as the more polar solvent.

4. Process of claim 1 wherein straight-chain or branched $C_1$ to $C_6$ alkylsulphones or cyclic sulphones of the formula

wherein
n is a number from 3 to 7, or lactams of the formula

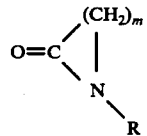

wherein
m is a number from 3 to 8 and
R is hydrogen or a $C_1$ to $C_6$ alkyl radical or ketones of the formula

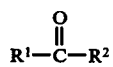

wherein
$R^1$ and $R^2$ are identical or different and represent straight-chain or branched $C_1$ to $C_6$ alkyl radicals or are linked via the group

wherein
o represents the numbers 4, 5, or 6, to form a ring, which optionally can be substituted by $C_1$ to $C_3$ alkyl radicals,
are used as the more polar solvent.

5. Process of claim 1 wherein sulpholane, -caprolactam or acetone is used as the more polar solvent.

6. Process of claim 1 wherein 1,5-dinitronaphthalene is separated off at 20° to 150° C.

7. Process of claim 1 wherein those compounds which at 20° C have a dielectric constant of 1.5 to 5.5 are used as the less polar aromatic solvent.

8. Process of claim 1 wherein compounds which at 20° C have a dielectric constant of 2 to 5 are used as the less polar aromatic solvent.

9. Process of claim 1 wherein aromatic compounds of the formula

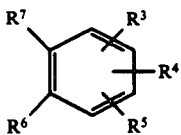

wherein
R$^3$ and R$^4$ and R$^5$ are the same or different and are hydrogen, chlorine or C$_1$ to C$_6$ alkyl and R$^6$ and R$^7$ are the same or different and are hydrogen or C$_1$ to C$_6$ alkyl or, conjointly with the groups —(CH$_2$)$_4$— or —(CH = CH)$_2$— are linked to form a ring which ring is optionally substituted by methyl and β or ethyl groups,
are used as the less polar solvent.

10. Process of claim 1 wherein toluene or oxylene is used as the less polar solvent.

11. Process of claim 1 wherein the treatment with a less polar solvent is carried out at a temperature of 40° to 150° C.

12. Process of claim 1 wherein 1,5-dinitronaphthalene is separated off by treatment with sulpholane and 1,8-dinitronaphthalene is separated off by treatement with toluene.

13. Process of claim 1 wherein in the first process step, the separation is carried out in the presence of 0.1 to 25 parts by weight of water.

14. Process of claim 1 wherein after 1,5-dinitronaphthalene has been separated off, a higher-boiling less polar solvent is added to the solution of the isomeric dinitronapthalenes in a more polar solvent and the more polar solvent is then distilled off.

15. Process of claim 1 wherein a mixture of isomeric dinitronaphthalenes which contains at least 10% and at most 98% of 1,5-dinitronaphthalene and at least 2% and at most 90% of 1,8-dinitronaphthalene is employed.

16. Process of claim 1 wherein in continuous operation, 1,5-dinitronaphthalene is substantially separated off as undissolved residue after treating a mixture of isomeric dinitronaphthalenes with a more polar solvent, in a first process tep, and, after separating off the more polar solvent, 1,8-dinitronaphthalene is substantially separated off as undissolved residue after treating the residual mixture of isomers with a less polar aromatic solvent at elevated temperature, in a second process step, and part or a substantial amount of the dinitronaphthalenes which have not yet been separated off are then fed back into the first process step.

* * * * *